United States Patent
Osypka

(10) Patent No.: US 10,758,217 B2
(45) Date of Patent: Sep. 1, 2020

(54) IMPLANTABLE SEALING DEVICE

(71) Applicant: Peter Osypka Stiftung, Grenzach-Wyhlen (DE)

(72) Inventor: Peter Osypka, Grenzach-Wyhlen (DE)

(73) Assignee: Peter Osypka Stiftung, Grenzach-Wyhlen (DE)

( * ) Notice: Subject to any disclaimer, the term of this patent is extended or adjusted under 35 U.S.C. 154(b) by 369 days.

(21) Appl. No.: 15/816,217

(22) Filed: Nov. 17, 2017

(65) Prior Publication Data

US 2018/0070934 A1 Mar. 15, 2018

Related U.S. Application Data

(62) Division of application No. 14/101,013, filed on Dec. 9, 2013, now abandoned.

(30) Foreign Application Priority Data

Dec. 10, 2012 (EP) .................................. 12008240

(51) Int. Cl.
*A61B 17/00* (2006.01)
*A61N 1/05* (2006.01)

(52) U.S. Cl.
CPC ........ *A61B 17/0057* (2013.01); *A61N 1/0587* (2013.01); *A61B 2017/00243* (2013.01);
(Continued)

(58) Field of Classification Search
CPC .. A61N 1/0587; A61N 1/0592; A61N 1/0595; A61B 2017/00615; A61B 2017/00597; A61B 2017/00592; A61B 2017/00575; A61B 2017/00606; A61B 2017/00623; A61B 2017/00637; A61B 17/0057; A61B 2017/00243;
(Continued)

(56) References Cited

U.S. PATENT DOCUMENTS

| | | |
|---|---|---|
| 2004/0220610 A1 | 11/2004 | Kreidler et al. |
| 2005/0177182 A1 | 8/2005 | van der Burg et al. |
| 2006/0229670 A1 | 10/2006 | Bates |
| 2007/0208376 A1 | 9/2007 | Meng |
| 2008/0033425 A1 | 2/2008 | Davis et al. |
| 2008/0200945 A1 | 8/2008 | Amplatz et al. |

(Continued)

FOREIGN PATENT DOCUMENTS

| | | | |
|---|---|---|---|
| DE | 202010011724 U1 * | 11/2010 | ......... A61B 17/0057 |
| DE | 202010011724 U1 | 11/2010 | |

(Continued)

OTHER PUBLICATIONS

European Search Report dated May 29, 2013 issued on corresponding European Patent Application No. 12008240.9 filed Dec. 10, 2012.

*Primary Examiner* — Katherine H Schwiker

(74) *Attorney, Agent, or Firm* — Locke Lord LLP; Scott D. Wofsy

(57) ABSTRACT

An implantable sealing device is disclosed herein and includes an elongated elastic member having distal and a proximal ends, at least one sealing element including braiding having outside and inside faces. The braiding can include of a plurality of fine threads of a memory metal alloy and wherein at least one face of the braiding is coated by a membrane. The braiding can also include a fixing member positioned at one of the distal and proximal ends of the elastic member and being positioned opposite to the braiding.

1 Claim, 5 Drawing Sheets

(52) U.S. Cl.
CPC ............... *A61B 2017/00575* (2013.01); *A61B 2017/00579* (2013.01); *A61B 2017/00592* (2013.01); *A61B 2017/00597* (2013.01); *A61B 2017/00615* (2013.01); *A61B 2017/00623* (2013.01); *A61B 2017/00867* (2013.01)

(58) Field of Classification Search
CPC   A61B 2017/00584; A61B 2017/00588; A61B 2017/00601; A61B 2017/00619; A61B 2017/00628; A61B 2017/00632; A61B 2017/00641; A61B 2017/00646; A61B 2017/00654; A61B 2017/00659
See application file for complete search history.

(56) References Cited

U.S. PATENT DOCUMENTS

| | | | | |
|---|---|---|---|---|
| 2011/0066180 | A1* | 3/2011 | Zeng | A61B 17/0057 606/213 |
| 2013/0178908 | A1* | 7/2013 | Huber | A61N 1/0592 607/14 |

FOREIGN PATENT DOCUMENTS

| | | | | |
|---|---|---|---|---|
| EP | 2340770 | A1 | 7/2011 | |
| WO | 2011/156782 | A1 | 12/2011 | |
| WO | WO-2011156782 | A1 * | 12/2011 | ......... A61B 17/0057 |

* cited by examiner

IMPLANTABLE SEALING DEVICE

CROSS-REFERENCE TO RELATED APPLICATIONS

This application is a divisional of U.S. patent application Ser. No. 14/101,013 filed Dec. 9, 2013, which claims priority under 35 U.S.C. § 119(a) to European Patent Application No. EP12008240, filed with the European Patent Office on Dec. 10, 2012, the content of each of which is incorporated by reference herein in its entirety.

BACKGROUND OF THE INVENTION

1. Field of the Invention

The present disclosure relates to an implantable sealing device for sealing a tissue opening, more specifically a trocar tube opening in the left ventricle of the heart.

2. Description of Related Art

Deficient heart valves can be repaired or replaced using a variety of different types of heart valve surgeries. One general type of heart valve surgery involves an open-heart surgical procedure during which the heart is stopped and blood flow is controlled by a heart-lung bypass machine. This type of valve surgery is highly invasive and exposes the patient to a number of potential risks associated with use of the heart-lung machine.

Due to the drawbacks of open-heart surgical procedures, there has been an increased interest in minimally invasive and percutaneous replacement of cardiac valves. Such surgical techniques involve making a relatively small opening in the chest of the patient into which a valve assembly is inserted and delivered into the heart via the operating device of a so-called trocar tube. The minimally invasive methods include reduced pain due to smaller incisions and less bleeding, shorter recovery time, and, especially, avoid the use of a heart-lung machine.

Minimally invasive surgical procedures such as transcatheter aortic valve implantation (TAVI) and transapical aortic valve implantation (TAAVI) have become feasible alternatives to open techniques in high risk patients.

In the TAVI process, the artificial valve is attached to a compressed stent, the stent being attached to a balloon catheter. The balloon catheter is inserted in the femoral artery and guided into the heart to the area of the aortic valve. Once in position, the balloon is inflated to secure the valve in place.

In the TAAVI approach, the replacement valve is inserted through a small incision in the chest wall of a patient and the catheter is advanced through the apex of the heart. Like in the TAVI approach, a balloon catheter is inserted through an introducer, e.g. a trocar tube and guided into the heart to the area of the aortic valve. After valve deployment, the trocar tube is removed and the opening in the ventricular apex is sutured.

A problem in the transapical procedure is the haemostatic closure of the left ventricular apex. Frequently, a purse string suture is placed in the tissue prior to insertion of the trocar tube to facilitate closure after the procedure is complete. After removing the trocar tube the ends of the suture are drawn tight to close the wound. Due to the high pressure created by the contraction of the heart severe problems may occur when the suture is not tight or disrupts.

SUMMARY OF THE INVENTION

An object of the present disclosure is therefore to provide an improved device for sealing a tissue opening, especially a trocar tube opening in the myocardium after the transapical procedure of valve replacement. The device can not only seals the tissue opening itself, such that the primary bleeding is stopped, but also prevent secondary bleeding from occurring. The tissue opening should be tightly closed. Furthermore, the device is filigree and flexible in order to be able to follow the movement of the heart without the occurrence of structural damage such as e.g. cracks. The beating of the heart and the heart rate of the patient should not be affected. Due to its filigree construction the braiding can take the anatomical shape of the apex of the left ventricle, the place where the trocar is introduced.

A further object of the disclosure is to provide the above required device and to simultaneously provide a possibility to place heart wires in minimally invasive heart surgery procedures.

The sealing device can include a membrane coated braiding of fine threads. Furthermore a tensioning member and a fixing member are present for placing and anchoring the sealing device into the myocardium.

In some embodiments, a sealing device according to the present disclosure comprises an elongated elastic member having a distal and a proximal end, at least one sealing element in form of an umbrella shaped braiding having outside and inside faces, the braiding being positioned respectively at the distal and proximal ends of the elastic member, wherein the braiding includes a plurality of fine threads of a memory metal alloy and wherein at least one face of the braiding is coated by a membrane, and a fixing member being positioned respectively at the distal and proximal ends of the elastic member and being positioned opposite to the braiding.

The braiding may be very soft and flexible in order to avoid injuring the very soft heart tissue. The braiding is able to follow the movement of the heart. The braiding is adapted to the anatomical shape of the apex of the left ventricle and includes at least 30 fine threads, preferably 30 to 100 threads, more preferably 70 to 90 threads. The threads are 0.03 to 0.15 mm in diameter, preferably 0.05 to 0.13 mm in diameter; more preferably circa 0.1 mm in diameter. Due to the number of fine threads the device fulfills the requirement of flexibility and softness.

The umbrella shaped braiding is preferably made out of Nitinol threads thus allowing the self-deployment of the membrane coated braiding whereby the braiding is adapted to the shape of the apex of the left ventricle due to the shape memory properties of Nitinol.

The interaction of the sealing member, the elastic member, and the fixing member allows the immediate closure of the opening in the apex of the left ventricle. The immediate closure is beneficial due to the high pressure in the left ventricle created by the contraction of the heart and the strong movement of the heart. The sealing of the trocar tube opening in the myocardium starts immediately after the placing and fixing of the membrane coated braiding.

A preferred sealing device comprises an elongated elastic member having distal a and a proximal end, at least one sealing element in form of an umbrella shaped braiding having outside and inside faces, the braiding being positioned respectively at the distal and proximal ends of the elastic member, wherein the braiding includes at least 30 threads made of Nitinol, said threads being 0.03 to 0.15 mm in diameter and wherein at least one face of the braiding is coated by a membrane, and whereby in a position in use the braiding is adapted to the anatomical shape of the apex of the left ventricle, and a fixing member positioned respectively at the distal and proximal ends of the elastic member and being positioned opposite to the braiding.

At least one membrane coated braiding can be present. When additional sealing may be necessary a second membrane coated braiding may be present positioned opposite to the first membrane coated braiding.

The membrane coated braiding is preferably positioned at the distal end of the elastic member, thus being positioned at the inner side of the opening in the myocardium in the position of use as shown in FIG. 2.

Suitable membranes are made out of biocompatible plastic such as e.g. silicone or polyurethane, preferably silicone. It is important that the membrane is biocompatible and impervious to blood.

The coating is positioned respectively at the outside face or at inside face of the braiding, preferably at the outside face. If desired, both sides of the braiding may be coated.

The elongated elastic member is a tensioning element and may be a spring or a member made from elastic biocompatible material like rubber. The spring is preferably a coil spring made, for example, from stainless steel, MP35N or Nitinol.

The fixing member may be any known fixing member which may be deployed from a retracted to an extended position. Preferably the fixing member includes radially expandable arms, e.g. a pair of radially expandable arms which extend from the elongated elastic member. The arms are formed from a bio-compatible material, such as stainless steel, MP35N or Nitinol, preferably Nitinol. The fixing member is operatively associated with the elongated elastic member and is mounted for movement between a retracted position wherein the arms are disposed within the interior lumen of the trocar tube and an extended position wherein the arms extend radially outwardly to anchor the elastic member and thus to anchor the umbrella shaped membrane coated braiding in the myocardium thus sealing the opening in the myocardium. The radially expandable arms may be different in shape, whereby the shape may influence the anchor effect. Before use, the sealing device is folded and is disposed within the interior lumen of the trocar tube.

The disclosure further relates to a method for sealing a tissue opening, especially a trocar tube opening in the myocardium at the apex of the left ventricle comprising inserting a trocar tube including a folded sealing device as described herein and guiding the trocar tube through an opening in the myocardium into the patient's left ventricle, pushing the folded umbrella shaped and membrane coated braiding out of the trocar tube so that the umbrella moves from a folded into a deployed position whereas the fixation member remains inside the trocar tube, stretching the elastic member by means of a tensioning cord and pulling the pre-stretched elastic member out of the opening in the myocardium whereby the fixing member is placed against the tissue of the myocardium and moves from a folded into a deployed position, removing the trocar tube whereby the elastic member remains stretched, and removing the tension from the elastic member whereby the fixing member anchors in the tissue of the myocardium.

These and other features of the systems and methods of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION OF THE INVENTION

Figure 1:
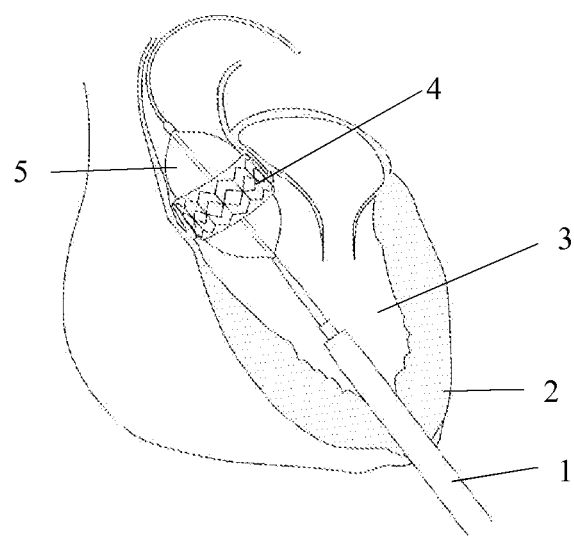
FIG. 1 is a schematic illustration of the transapical valve insertion technique.

Reference will now be made to the drawings wherein like reference numerals identify similar structural features or aspects of the subject disclosure. FIG. 1 is a schematic illustration of the transapical valve insertion technique and shows the balloon catheter used to insert new artificial heart valves during Transapical Aortic Valve Implantation (TAAVI) according to the state of the art. Trocar tube 1 is inserted into the left ventricle 3 of the heart through the myocardium 2. A compressed valve prosthesis constructed from a stainless steel stent with an attached artificial valve 4 is placed on the balloon catheter 5, inserted into the apex of the left ventricle, and positioned directly inside the diseased aortic valve. Once in position, the balloon is inflated to secure the valve in place. The balloon is then deflated and removed leaving the new valve to function immediately.

Figure 2:
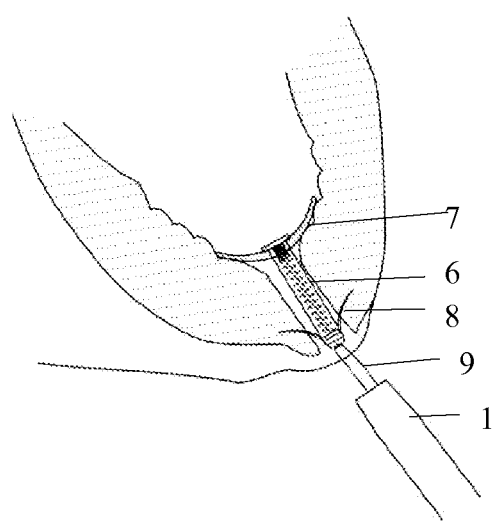
FIG. 2 shows the sealing device, sealing the inner myocardium.

FIG. 2 shows the sealing device sealing the opening in the myocardium. Trocar tube 1, via which the sealing device had been inserted, is retracted behind the ventricular apex. The opening in the tissue is tightly sealed by the membrane coated braiding 7 which is positioned at the inner myocardium at the distal end of the elastic member 6. As shown in the embodiment of FIG. 2, the elastic member 6 includes a coil spring. The braiding 7 is adapted to the anatomical shape of the apex of the left ventricle.

The flexible braiding 7 tightly closes the inner tissue of the heart and is anchored by the fixing member which is operatively associated with the coil spring of elastic member 6. The coil spring is stretched by pulling the double thread 9 down. After the placement of the sealing device, the thread 9 may be removed by pulling down one side of the thread 9 so that the thread 9 may slip out.

Figure 3:
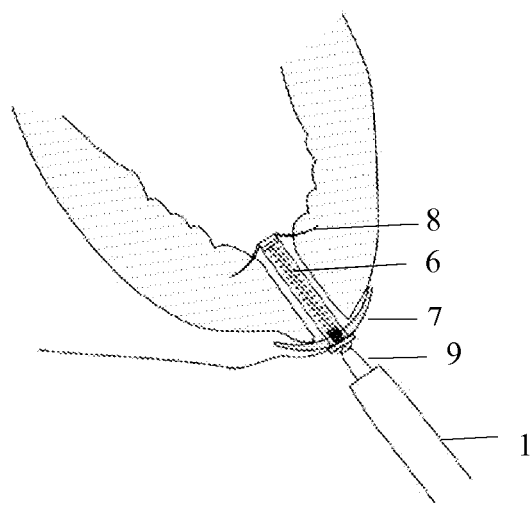
FIG. 3 show the sealing device, sealing the outer myocardium.

FIG. 3 shows the sealing device sealing the outer myocardium. The sealing device can be positioned the other way around as described above should the anatomical shape of the left ventricular apex not allow sealing of the inner myocardium. In this case the membrane coated braiding 7 is positioned at the outer myocardium.

Figure 4:
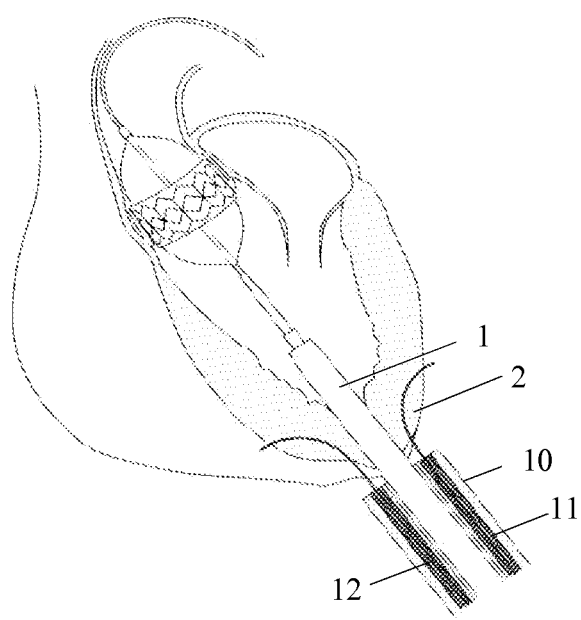
FIG. 4 is a view corresponding to FIG. 1 and in addition shows temporary electrodes inserted for heart stimulation.
Figure 5A:
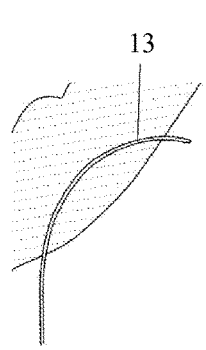
FIGS. 5a to 5d show the placing and the affixing of the stimulation electrodes.
Figure 5B:
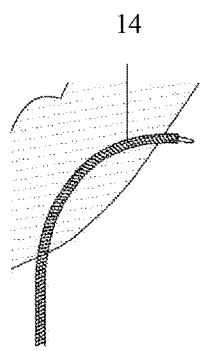
Figure 5C:
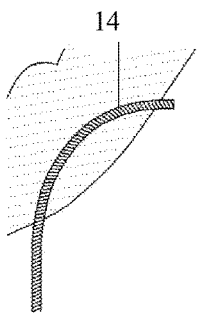
Figure 5D:
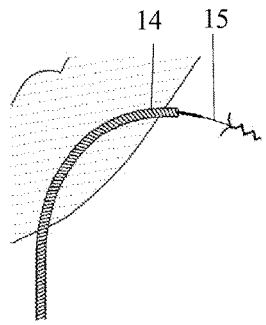

FIG. 4 is a view corresponding to FIG. 1 and in addition shows temporary electrodes (heart wires) inserted for heart stimulation. Heart wires are normally placed in open heart surgical procedures and are attached to the epicardium to synchronize the heart after the surgery. The embodiment according to FIG. 4 provides a possibility to attach heart wires even if the heart is not exposed.

An additional catheter 10 is slipped over the trocar tube 1. The catheter 10 is a three-lumen device which comprises a tubular body defining a first inner lumen extending longitudinally there-through for slipping the catheter over the trocar tube and a second and third lumen 11, 12 which run along each side of the inner lumen allowing temporary electrodes to pass therethrough. A Nitinol-stylet 13, which is preferably pre-shaped, is first inserted within said lumen for assisting in steering of the stimulation electrode when implanted.

FIGS. 5*a* to 5*d* show insertion of an electrode within the myocardium of the heart. A pre-shaped stylet 13 is first inserted within lumen 11 or 12 and guided from outside of the heart into and through the myocardium. The tip of the stylet 13 leaves the tissue of the myocardium. A coil 14 is then guided over the stylet towards its tip. The stylet 13 is then withdrawn and the temporary electrode 15 is inserted via the lumen of the coil 14. The proximal portion of electrode 15 is connected to an external pacemaker. The stimulating procedure is the same procedure as the placing of heart wires which are used in open heart surgical procedures if it is expected that the patient will need stimulation for a limited time after the surgery. After completion of temporary stimulation the heart wires are removed by pulling.

Figure 6:
FIG. 6 shows a stimulation electrode in detail.

FIG. 6 shows a stimulation electrode comprising, at its distal end, a loop 16 and a fixing member. The stimulation electrode is inserted by means of coil 17.

Figure 7A:
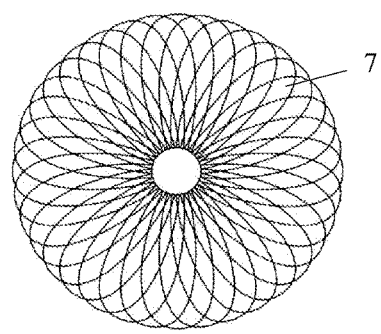
FIGS. 7a, 7b and 7c show the sealing system in detail.
Figure 7B:
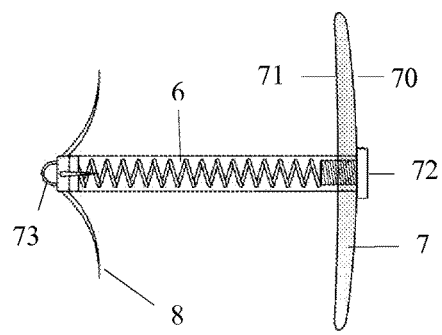
Figure 7C:
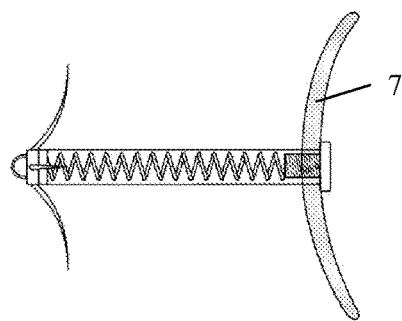

FIGS. 7*a*, 7*b* and 7*c* show the sealing system in detail. FIG. 7*a* is a top view of the umbrella shaped braiding 7. In some embodiments, the braiding can include about 80 Nitinol threads having a diameter of about 0.1 mm. FIG. 7*b* is a side view of the sealing device. Coil spring of elastic member 6 is attached to the braiding 7 at its distal end. The fixing member 8 is operatively associated with the coil spring at its proximal end. Loop 73 allows double thread 9 to pass therethrough. Socket 72 may hold the ends of the braiding threads. In unfolded condition the braiding 7 can be umbrella shaped or any other suitable shape. The coating is positioned at the outside face 70 or at the inside face 71 of the braiding 7, preferably at the outside face. If desired, both sides of the braiding 7 may be coated. FIG. 7*c* shows the braiding 7 in the shape adapted to the anatomical shape of the apex of the left ventricle as shown in use in FIG. 2.

Figures 8, 9, 10:
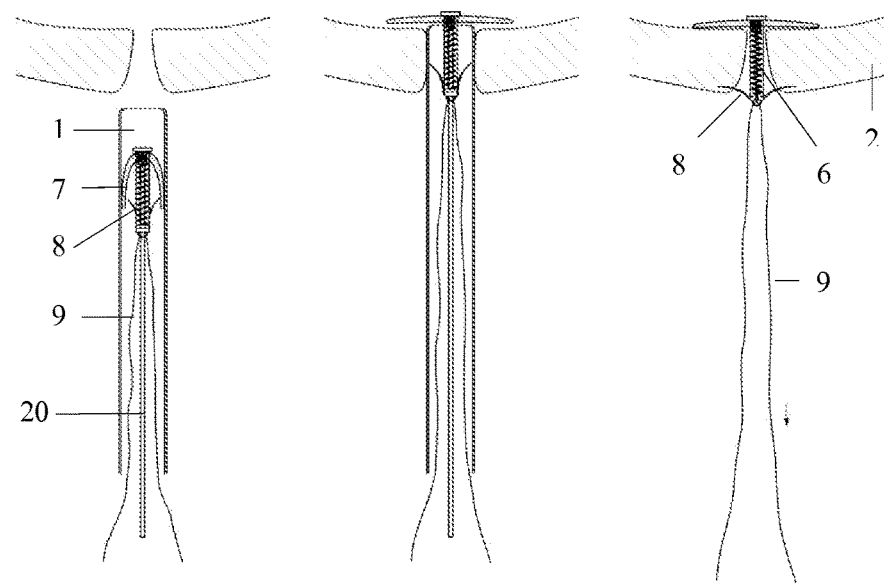
FIGS. 8, 8a, 9, 9a and 10, 10a, show the steps of placing and affixing the sealing system.

FIGS. 8, 9, and 10 show the steps of placing and affixing the sealing system. FIG. 8 shows the sealing device positioned inside trocar tube 1 before placing the device into the left ventricle. Braiding 7 and fixing member 8 are folded. The stick 20 is for pushing out the sealing device. The folding may be upwards (FIG. 8) or downwards (FIG. 8*a*).

Figures 8A, 9A, 10A:
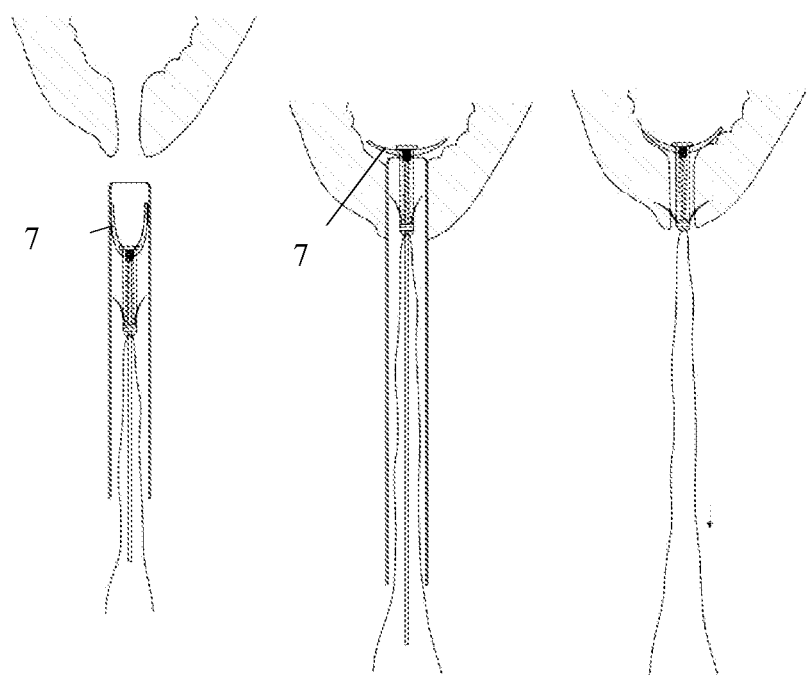

FIGS. 9 and 9*a* show the trocar tube placed in the myocardium functioning as a portal for the subsequent placement of the sealing device. The braiding 7 is pushed out of the trocar tube 1 and is unfolded. The fixing member 8 is inside the tube 1 and thus still protected. FIG. 9 and FIG. 9*a* differ in the anatomical shape of the apex of the left ventricle and show the adaption of the shape of the braiding 7 to the different anatomical shapes.

FIGS. 10 and 10*a* show the sealing device placed and the trocar tube 1 removed. By pulling double thread 9 downwards coil spring of the elastic member 6 is pre-stretched. The pre-stretched coil spring is pulled downwards out of the opening in the myocardium. After removing the trocar tube 1 whereby the double thread is still stretched the fixing member 8 moves from a folded into a deployed position and anchors in the myocardium tissue.

While the apparatus and methods of the subject disclosure have been shown and described with reference to embodiments, those skilled in the art will readily appreciate that changes and/or modifications may be made thereto without departing from the spirit and scope of the subject disclosure.

What is claimed is:

1. A method for sealing an apical access opening of a left ventricle previously created by a trocar tube and for simultaneous cardiac pacing, the method comprising:
    inserting a trocar tube within a patient's left ventricle and guiding the trocar tube under an aortic valve to be replaced;
    slipping a three lumen catheter over the trocar tube, the catheter including a tubular body defining a first inner lumen extending longitudinally there through for slipping the catheter over the trocar tube and a second and third lumen which run along each side of the inner lumen respectively allowing temporary electrodes to pass therethrough,
    inserting a pre-shaped stylet in the second lumen and in the third lumen and guiding the stylet through a myocardium;
    inserting temporary myocardial electrodes in the second lumen and in the third lumen and guiding the electrodes via the stylet to both sides of a left ventricle apex;
    connecting the electrodes to an external pacemaker;
    performing high frequency ventricular pacing with the electrodes;
    inserting a balloon catheter through the trocar tube to expand the aortic valve to be replaced;
    implanting new aortic valve;
    reducing the heart rate with the electrodes; and
    withdrawing the trocar tube partly to the left ventricle apex and inserting a sealing device comprising:
        i) an elongate elastic member having a distal end and a proximal end;
        ii) at least one sealing element having an umbrella shaped braiding with outside and inside faces, the braiding extending radially from the elastic member, the braiding being positioned at the distal end of the elastic member, wherein the braiding includes a plurality of threads of shape memory metal alloy and wherein at least one face of the braiding is coated by a membrane;
        a fixing member positioned at the proximal end of the elastic member opposite to the braiding; and
        a double thread positioned at the proximal end of the elastic member;
    wherein the sealing device is inserted by
        pushing the braiding out of the trocar tube so that the braiding moves from a folded umbrella configuration into a deployed umbrella configuration whereas the fixing member remains inside the trocar tube;
        stretching the elastic member by using the double thread, pulling the trocar tube down beneath the left ventricle apex whereby the elastic member remains stretched, and pulling the stretched elastic member out of the apical opening whereby the fixing member moves from a folded position into a deployed position;
        removing tension from the elastic member whereby the fixing member anchors to a tissue of the myocardium; and
        removing the trocar tube completely from the patient.

* * * * *